United States Patent
Marks et al.

(10) Patent No.: US 9,416,070 B2
(45) Date of Patent: Aug. 16, 2016

(54) FORMING ETHYLENE

(71) Applicant: Northwestern University, Evanston, IL (US)

(72) Inventors: Tobin J. Marks, Evanston, IL (US); Chao Xie, Knoxville, TN (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/413,465

(22) PCT Filed: Jul. 18, 2013

(86) PCT No.: PCT/US2013/051070
§ 371 (c)(1),
(2) Date: Jan. 8, 2015

(87) PCT Pub. No.: WO2014/015132
PCT Pub. Date: Jan. 23, 2014

(65) Prior Publication Data
US 2015/0175503 A1    Jun. 25, 2015

Related U.S. Application Data

(60) Provisional application No. 61/672,802, filed on Jul. 18, 2012.

(51) Int. Cl.
| | |
|---|---|
| *C07C 2/84* | (2006.01) |
| *B01J 37/20* | (2006.01) |
| *B01J 21/06* | (2006.01) |
| *B01J 23/44* | (2006.01) |
| *B01J 35/00* | (2006.01) |

(52) U.S. Cl.
CPC ............... *C07C 2/84* (2013.01); *B01J 21/066* (2013.01); *B01J 23/44* (2013.01); *B01J 35/002* (2013.01); *B01J 37/20* (2013.01); *C07C 2521/06* (2013.01); *C07C 2527/045* (2013.01); *Y02P 20/52* (2015.11)

(58) Field of Classification Search
CPC .......... B01J 23/44; B01J 37/20; B01J 21/066; B01J 35/002; C07C 2/84; C07C 11/04; C07C 2521/06; C07C 2527/045; Y02P 20/52
See application file for complete search history.

(56) References Cited

U.S. PATENT DOCUMENTS

| | | |
|---|---|---|
| 2007/0073083 A1 | 3/2007 | Sunley |
| 2010/0331595 A1 | 12/2010 | Chinta et al. |
| 2014/0200383 A1* | 7/2014 | Marks et al. ............... C07C 2/84 585/658 |

FOREIGN PATENT DOCUMENTS

| | | |
|---|---|---|
| EP | 0210383 | 2/1987 |
| WO | 2004103936 | 12/2004 |

OTHER PUBLICATIONS

J.R. Anderson, et al., "Reaction of Methane and Sulfur: Oxidative Coupling and Carbon Disulfide Formation" React. Kinet. Catal. Lett., vol. 49, No. 2, 261-269, (1993) (9 pgs).

L.P. Didenko, et al., "Partial Catalytic Oxidation and Condensation of Methane by Oxygen and Sulphur" Catalysis Today 42 (1998) 367-370 (4 pgs).

International Search Report and Written Opinion for related PCT Application PCT/US2013)051070, mailed Aug. 29, 2013 (10 pgs).

\* cited by examiner

*Primary Examiner* — Nathan M Nutter
(74) *Attorney, Agent, or Firm* — Brooks, Cameron & Huebsch, PLLC

(57) ABSTRACT

A method that includes forming ethylene from methane including contacting supported-palladium with hydrogen sulfide to form a palladium sulfide catalyst and contacting the palladium sulfide catalyst with methane to form ethylene.

8 Claims, 3 Drawing Sheets

FORMING ETHYLENE

This application is a National Stage Application under 35 U.S.C. §371 of International Application Number PCT/US2013/051070, filed Jul. 18, 2013 and published as WO 2014/015132 on Jan. 23, 2014, which claims the benefit to U.S. Provisional Application 61/672,802, filed Jul. 18, 2012, the entire contents of which are incorporated herein by reference in its entirety.

This disclosure relates to methods of forming ethylene, and in particular forming ethylene from methane.

Ethylene is a commodity chemical that is used as a building block for the chemical industry. Ethylene is used to manufacture products including, but not limited to, food packaging, eyeglasses, cars, medical devices, lubricants, engine coolants, and liquid crystal displays.

One current process of ethylene formation is oxidative methane coupling employing oxygen as an oxidant. In this oxidative methane coupling process, methane is activated heterogeneously on a catalyst surface and generally thought to form methyl free radicals, which then couple in the gas phase to form ethane. The ethane subsequently undergoes dehydrogenation to form ethylene. However, oxidative methane coupling employing oxygen as the oxidant has shown poor selectively to ethylene formation, as well as undesirable over-oxidation to carbon dioxide.

Figure 1:
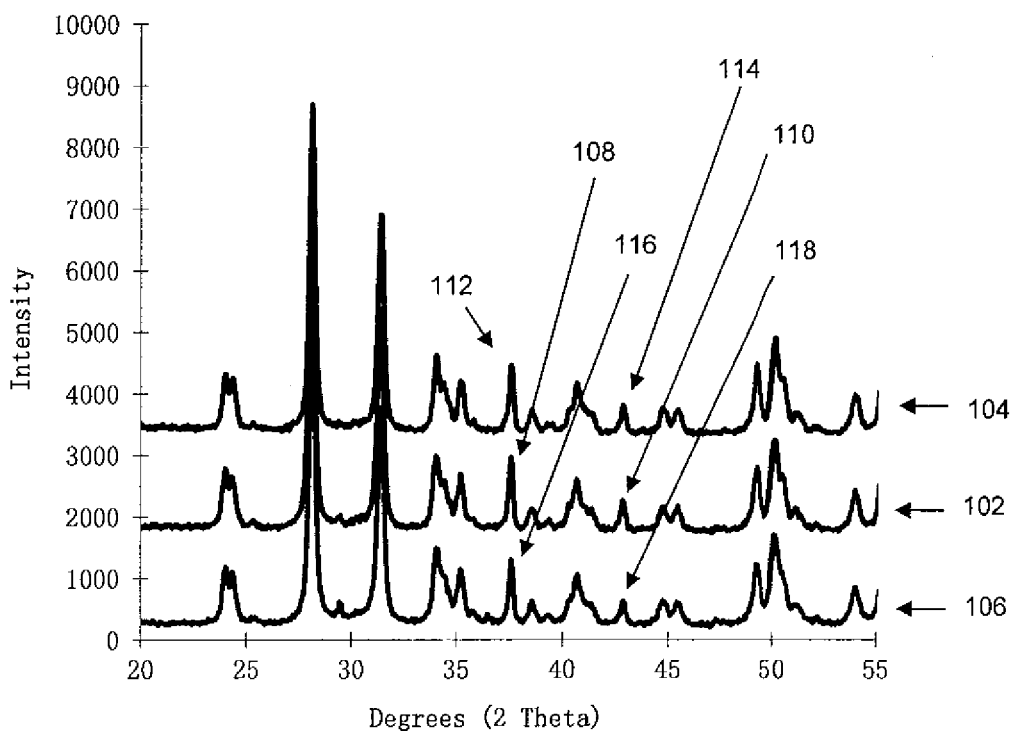
FIG. 1 illustrates scans obtained via x-ray diffraction of portions of palladium sulfide catalysts. The scans illustrated in FIG. 1 illustrate curves, which represent intensity, in counts per second (cps), versus degrees (2 theta).

This disclosure provides a method of forming ethylene from methane including contacting supported-palladium with hydrogen sulfide to form a palladium sulfide catalyst and contacting the palladium sulfide catalyst with methane to form ethylene. Advantageously, the method provides desirable methane conversion and ethylene selectivity.

The method includes contacting supported-palladium with hydrogen sulfide. The supported-palladium may be referred to as a catalyst precursor. A support for the supported-palladium is selected from the group consisting of $MO_2$, cerium oxide ($CeO_2$), silicon oxide ($SiO_2$), magnesium oxide (MgO), $Ln_2O_3$, aluminum oxide ($Al_2O_3$), $Li_2O$, or a combination thereof, where M is Ti, Zr, Hf, or a combination thereof, and Ln is a lanthanide element, Y, Sc, or a combination thereof. The palladium can be from 1 weight percent to 50 weight percent of total weight of the palladium and the support.

The method conditions include a weight hourly space velocity (WHSV), which is defined as a mass flow rate of a feed, e.g., hydrogen sulfide ($H_2S$) or methane, per mass of catalyst or catalyst precursor, e.g., palladium sulfide catalyst or supported-palladium. For example, the WHSV may be calculated as a mass of the methane in grams per hour divided by a mass of the palladium sulfide catalyst in grams or may be calculated as a mass of $H_2S$ in gram per hour divided by a mass of the supported-palladium.

$H_2S$ can contact the supported-palladium at a temperature in range of from 0 degrees Celsius (° C.) to 2000° C. Hydrogen sulfide ($H_2S$) can contact the supported-palladium at a preferred temperature within a range of from 200° C. to 1500° C. A volume of the $H_2S$ in mL per hour divided by a mass of the supported-palladium in grams has a value in a range of from 6000 $mL \cdot g^{-1} \cdot h^{-1}$ to 30000 $mL \cdot g^{-1} \cdot h^{-1}$. Hydrogen sulfide ($H_2S$) can contact the supported-palladium at an absolute pressure within a range of 101.32 kilopascals (KPa) to 1013.2 KPa.

Contacting the supported-palladium with the $H_2S$ forms a palladium sulfide catalyst. As used herein, the palladium sulfide catalyst can include palladium sulfides and/or palladium subsulfides, such as $Pd_4S$, $Pd_3S$ and/or $Pd_{16}S_7$.

The method includes contacting the palladium sulfide catalyst with methane to form ethylene. Methane can contact the palladium sulfide catalyst at a temperature in range of from 850° C. to 2000° C. Methane can contact the palladium sulfide catalyst at a preferred temperature in range of from 900° C. to 1500° C. A volume of the methane in mL per hour divided by a mass of the palladium sulfide catalyst in grams has a value in a range of from 6000 $mL \cdot g^{-1} \cdot h^{-1}$ to 30000 $mL \cdot g^{-1} \cdot h^{-1}$. Methane can contact the palladium sulfide catalyst at an absolute pressure in range of from 101.32 KPa to 1013.2 KPa.

The method may include supplying an inert carrier gas to transport at least one of the hydrogen sulfide and the methane, e.g., to the palladium sulfide catalyst. Examples of the inert carrier gas include, but are not limited to, argon, helium, nitrogen, or a combination thereof. A molar ratio of methane to $H_2S$ used in the present method can be in a range from 2.9 to 1 to 17.4:1. The molar ratio of methane to $H_2S$ used in the present method can also be in a range from 5 to 1 to 7:1.

EXAMPLES

Materials include: methane (Airgas, Inc.); argon (Airgas, Inc.); hydrogen sulfide (Sigma-Aldrich®); supported-palladium: $Pd/ZrO_2$ (10 weight percent palladium, Sigma-Aldrich®). Equipment includes a heterogeneous catalytic reactor system (Altamira Instruments) having a vapor generator, a rector preheater, and a tubular reactor.

Catalyst 1 Formation

Load supported-palladium (100 milligrams (mg)) into a tubular reactor (10 millimeter (mm) inner diameter). Purge the reactor system with argon (35 milliliters per minute (mL/min)) for one hour (hr). Maintain argon flow (35 mL/min) to the reactor system and heat reactor system components to experimental temperature (900° C.) at 10° C./min. Inject a hydrogen sulfide/argon mixture (1 volume percent hydrogen sulfide) into the reactor for 2 hrs at 25 mL/min while the reactor contents are maintained at the experimental temperature and an absolute pressure of 101.32 KPa to form a palladium sulfide catalyst (catalyst 1). Perform X-ray diffraction (XRD) on a portion of catalyst 1. The XRD indicates catalyst 1, which includes $Pd_{16}S_7$, is formed.

Catalyst 2 Formation

Repeat catalyst 1 formation, but with change: for catalyst 2 use an experimental temperature of 1000° C. instead of 900° C.

Catalyst 3 Formation

Repeat catalyst 1 formation, but with change: for catalyst 3 use an experimental temperature of 800° C. instead of 900° C.

FIG. 1 illustrates scans obtained via X-ray diffraction of portions of palladium sulfide catalysts. The scans illustrated in FIG. 1 illustrate curves, which represent intensity, in counts per second (cps), versus degrees (2 theta). In FIG. 1, curve 102 corresponds to catalyst 1, curve 104 corresponds to catalyst 2, and curve 106 corresponds to catalyst 3. The curve 102 delineates a peak 108 at approximately 37.6 degrees and a peak 110 at approximately 42.9 degrees that respectively correspond to $Pd_{16}S_7$, indicating that catalyst 1 is formed by contacting supported-palladium with hydrogen sulfide. Similarly, the curve 104 delineates a peak 112 at approximately 37.6 degrees and a peak 114 at approximately 42.9 degrees, indicating that catalyst 2 is formed, and the curve 106 delineates a peak 116 at approximately 37.6 degrees and a peak 118 at approximately 42.9 degrees, indicating that catalyst 3 is formed.

Example (Ex) 1

Load supported-palladium (100 mg) into a tubular reactor (10 mm inner diameter). Purge the reactor system with argon (35 mL/min) for one hr. Maintain argon flow (35 mL/min) to the reactor system and heat reactor system components to the desired experimental temperature (900° C.) at 10° C./min. Introduce a hydrogen sulfide/argon mixture (1 weight percent hydrogen sulfide) into the reactor for 2 hrs at 25 mL/min while the reactor contents are maintained at the experimental temperature and an absolute pressure of 101.32 KPa to form a palladium sulfide catalyst. Introduce a methane/argon mixture (10 volume percent methane) into the reactor at 15 mL/min while the reactor contents are maintained at the experimental temperature and an absolute pressure of 101.32 KPa to form ethylene. Maintain conditions for a period of time, and then separate and analyze the products with an Agilent 7890 Gas Chromatography system including a flame ionization detector, a thermal conductivity detector, and a flame photometric detector. The analysis indicates that ethylene, carbon disulfide, and hydrogen sulfide are formed.

Ex 2

Repeat Ex 2, but with change: for Ex 2 use an experimental temperature of 1000° C., instead of 900° C.

Comparative Example (Com Ex) A

Repeat Ex 1, but with change: for Com Ex A use an experimental temperature of 800° C., instead of 900° C.

Figure 2:
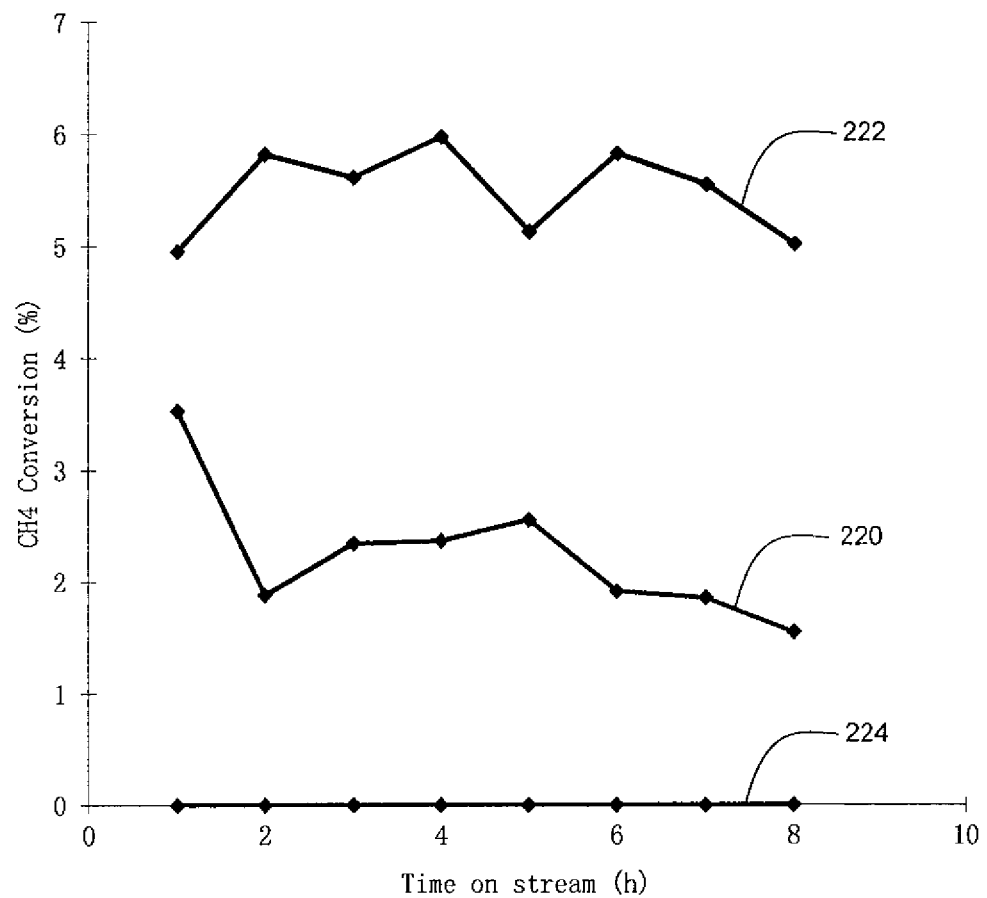
FIG. 2 illustrates a methane conversion versus time (hours) diagram associated with Example 1, Example 2, and Comparative Example A.

FIG. 2 illustrates a methane conversion versus time (hours) diagram associated with Ex 1, Ex 2, and Comp Ex A. Methane conversion for each of Ex 1, Ex 2, and Comp Ex A is calculated by the following formula:

$$\text{Methane conversion} = \frac{\text{moles } CH_{4(input)} - \text{moles } CH_{4(output)}}{\text{moles } CH_{4(input)}} \times 100\%$$

In FIG. 2, curve 220 corresponds to Ex 1, curve 222 corresponds to Ex 2, and curve 224 corresponds to Comp Ex A. Curve 220 illustrates that methane conversion occurs at 900° C. and curve 222 illustrates that methane conversion occurs at a relatively higher temperature of 1000° C. Curve 224 illustrates that methane conversion is negligible at 800° C.

Figure 3:
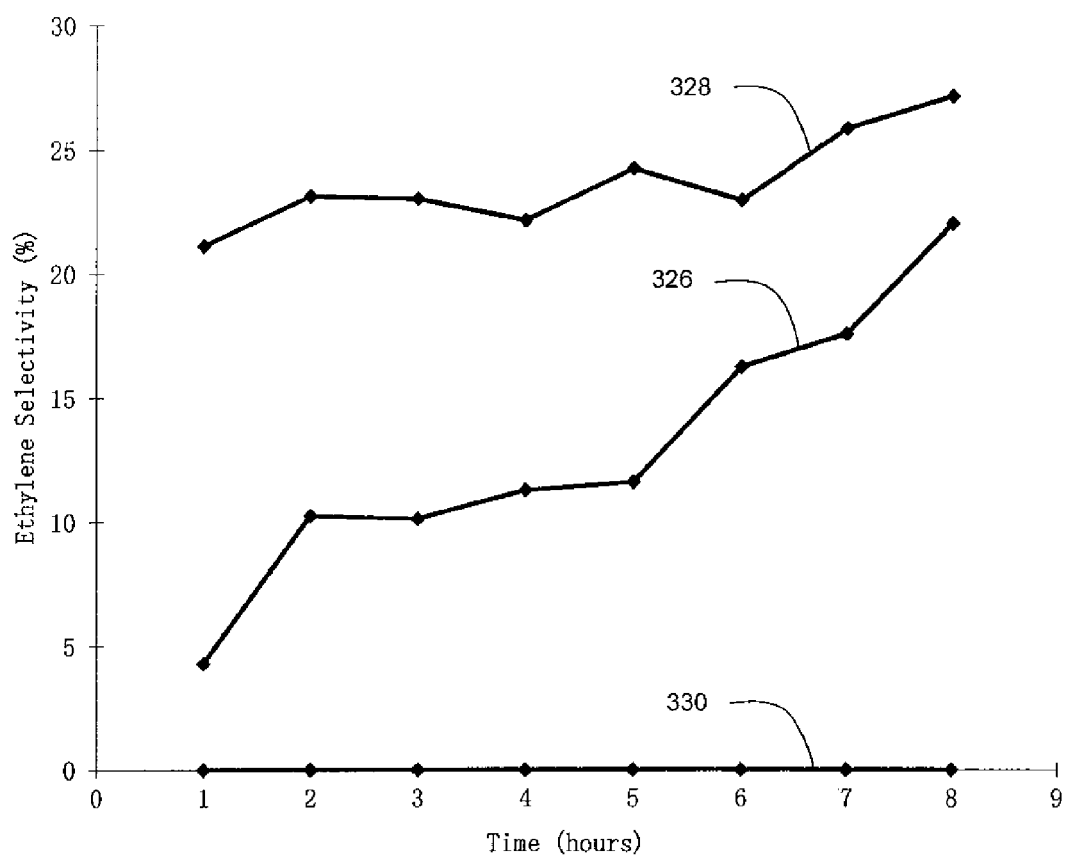
FIG. 3 illustrates an ethylene selectivity versus time (hours) diagram associated with Example 1, Example 2, and Comparative Example A.

FIG. 3 illustrates an ethylene selectivity versus time (hours) diagram associated with Ex 1, Ex 2, and Comp Ex A. Ethylene selectivity for each of Ex 1, Ex 2, and Comp Ex A is calculated by the following formula:

$$\text{Ethylene selectivity} = \frac{2 \times \text{moles } C_2H_{4(output)}}{\text{moles } CH_{4(input)} - \text{moles } CH_{4(output)}} \times 100\%$$

In FIG. 3, curve 326 corresponds to Ex 1, curve 328 corresponds to Ex 2, and curve 330 corresponds to Comp Ex A. Curve 326 illustrates that ethylene is selectivity formed at 900° C. and curve 328 illustrates that ethylene is selectivity formed at a relatively higher temperature of 1000° C. Curve 330 illustrates that ethylene formation is negligible at 800° C.

What is claimed:

1. A method of forming ethylene from methane comprising:
   contacting supported-palladium with hydrogen sulfide to form a palladium sulfide catalyst; and
   contacting the palladium sulfide catalyst with methane to form ethylene.

2. The method of claim 1, wherein a support for the supported palladium is selected from the group consisting of $MO_2$, cerium oxide ($CeO_2$), silicon oxide ($SiO_2$), magnesium oxide (MgO), $Ln_2O_3$, aluminum oxide ($Al_2O_3$), $Li_2O$, or a combination thereof, where M is Ti, Zr, Hf, or a combination thereof, and Ln is a lanthanide element, Y, Sc, or a combination thereof.

3. The method of claim 1, wherein the palladium sulfide catalyst includes $Pd_{16}S_7$.

4. The method of claim 1, wherein contacting supported-palladium with hydrogen sulfide to form a palladium sulfide catalyst occurs at a temperature in range of from 0 degrees Celsius to 2000 degrees Celsius.

5. The method of claim 1, wherein contacting the palladium sulfide catalyst with methane to form ethylene occurs at a temperature in range of from 850 degrees Celsius to 2000 degrees Celsius.

6. The method of claim 1, wherein a volume of the hydrogen sulfide in mL per hour divided by a mass of the supported-palladium in grams has a value in a range of from 6000 mL·g$^{-1}$·h$^{-1}$ to 30000 mL·g$^{-1}$·h$^{-1}$.

7. The method of claim 1, wherein a volume of the methane in mL per hour divided by a mass of the palladium sulfide catalyst in grams has a value in a range of from 6000 mL·g$^{-1}$·h$^{1}$ to 30000 mL·g$^{-1}$·h$^{-1}$.

8. The method of claim 1, further including supplying an inert carrier gas to transport at least one of the hydrogen sulfide and the methane.

* * * * *